US00PP22629P2

(12) United States Plant Patent
van Dijk

(10) Patent No.: US PP22,629 P2
(45) Date of Patent: Apr. 3, 2012

(54) ***ANTHURIUM* PLANT NAMED 'ANTHCASZIM'**

(50) Latin Name: ***Anthurium andreanum* L.**
Varietal Denomination: Anthcaszim

(75) Inventor: Jan van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 13/136,683

(22) Filed: Aug. 8, 2011

(51) Int. Cl.
*A01H 5/00* (2006.01)

(52) U.S. Cl. ..... Plt./365; Plt./367

(58) Field of Classification Search ..... Plt./365, Plt./367, 368
See application file for complete search history.

(56) References Cited

OTHER PUBLICATIONS

UPOV-ROM Plant Variety Database, PBR 20092518, published Feb. 15, 2010 in the European Community, one page.*

* cited by examiner

*Primary Examiner* — June Hwu
*Assistant Examiner* — Louanne Krawczewicz Myers
(74) *Attorney, Agent, or Firm* — Jondle & Associates, P.C.

(57) ABSTRACT

A new *Anthurium* plant particularly distinguished by having glossy pink, durable spathes that very slowly turn brown with age, dark green, durable glossy leaves, an erect penduncle, rich shoot formation, continuous flowering throughout the year, a compact and full plant habit, and a plant height of 40.0 cm to 55.0 cm, is disclosed.

3 Drawing Sheets

Genus and species: *Anthurium andreanum* L.
Variety denomination: 'Anthcaszim'.

BACKGROUND OF THE NEW PLANT

The present invention comprises a new and distinct variety of *Anthurium*, botanically known as *Anthurium andreanum* L., and hereinafter referred to by the variety name 'Anthcaszim'. The new variety originated from a spontaneous mutation from the variety 'Anthbneq' (U.S. Plant Pat. No. 15,286) in a large production clone of the variety 'Anthbneq' in a greenhouse in May 2005 in Bleiswijk, The Netherlands.

The female parent of the original variety 'Anthbneq' was a pink-colored *Anthurium* pot plant '634-01' (unpatented). The male parent was an orange-colored flowering *Anthurium* pot plant '532-02' (proprietary, unpatented). The original variety 'Anthbneq' was discovered and selected as a flowering plant from the progeny of the above cross in March, 1998 in a controlled environment in a glasshouse in Bleiswijk, The Netherlands.

The new variety 'Anthcaszim' was selected in May 2005 from a production clone of 'Anthbneq' and has been asexually reproduced repeatedly by tissue culture in Bleiswijk, The Netherlands over a four-year period. The new variety has been found to retain its distinctive characteristics through successive asexual propagations.

Plant Breeder's Rights for this variety were applied for in the European Union on Nov. 26, 2009, in Japan on Mar. 9, 2010, and in Korea on Jun. 7, 2010. 'Anthcaszim' has not been made publicly available or sold anywhere in the world for more than one year prior to the filing of this application.

SUMMARY OF THE INVENTION

The following are the most outstanding and distinguishing characteristics of this new variety when grown under normal horticultural practices in Bleiswijk, The Netherlands.

1) A pink medium sized glossy spathe;
2) White spadix;
3) Compact plant habit; and
4) Dark green glossy foliage.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 48-week old plant grown in a greenhouse in Bleiswijk, The Netherlands in 2009.

DESCRIPTION OF THE NEW VARIETY

Figure 1:
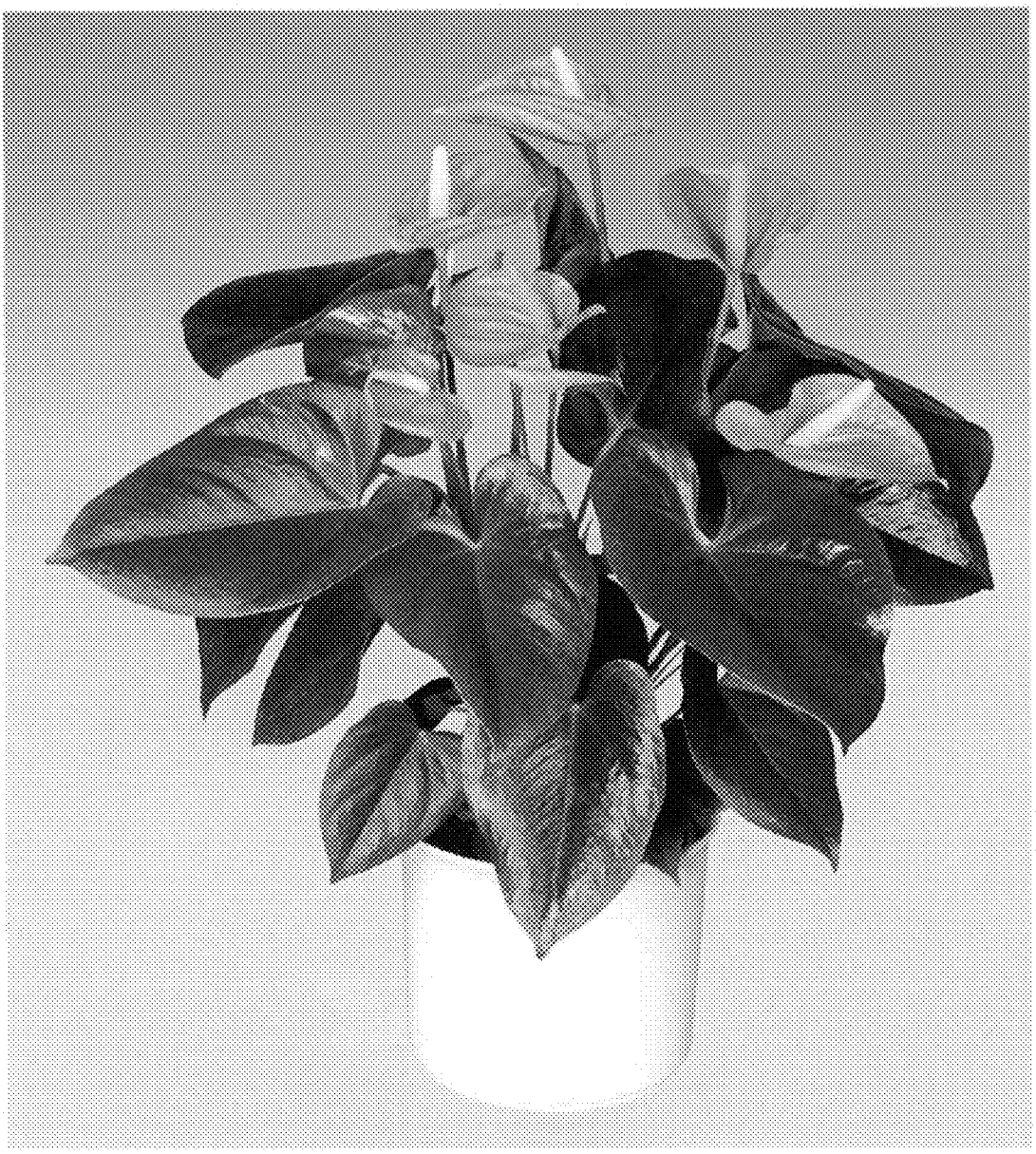
FIG. 1 shows the overall plant habit, including blooms, buds and foliage.
Figure 2:
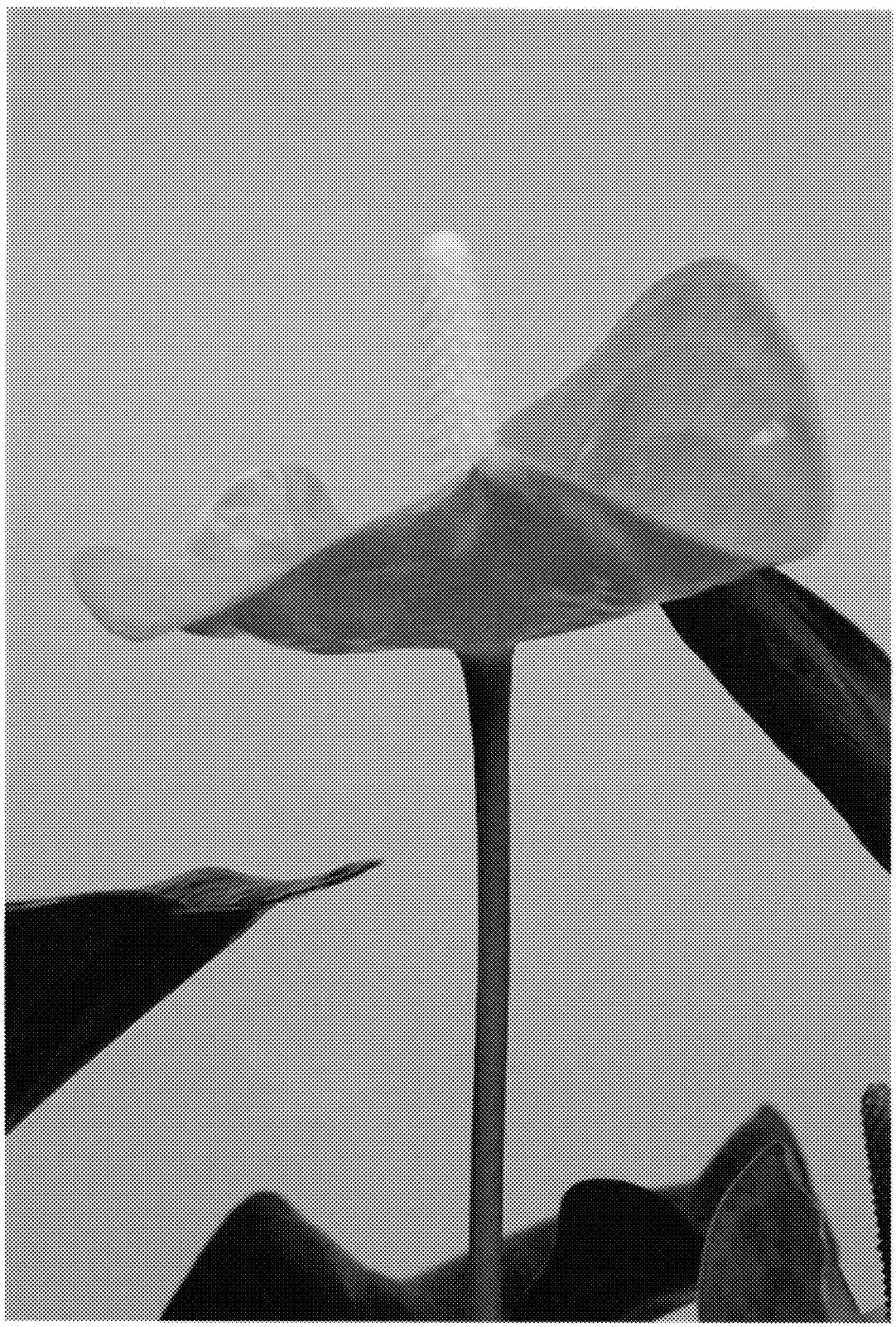
FIG. 2 is a close-up of the mature spathe.
Figure 3:
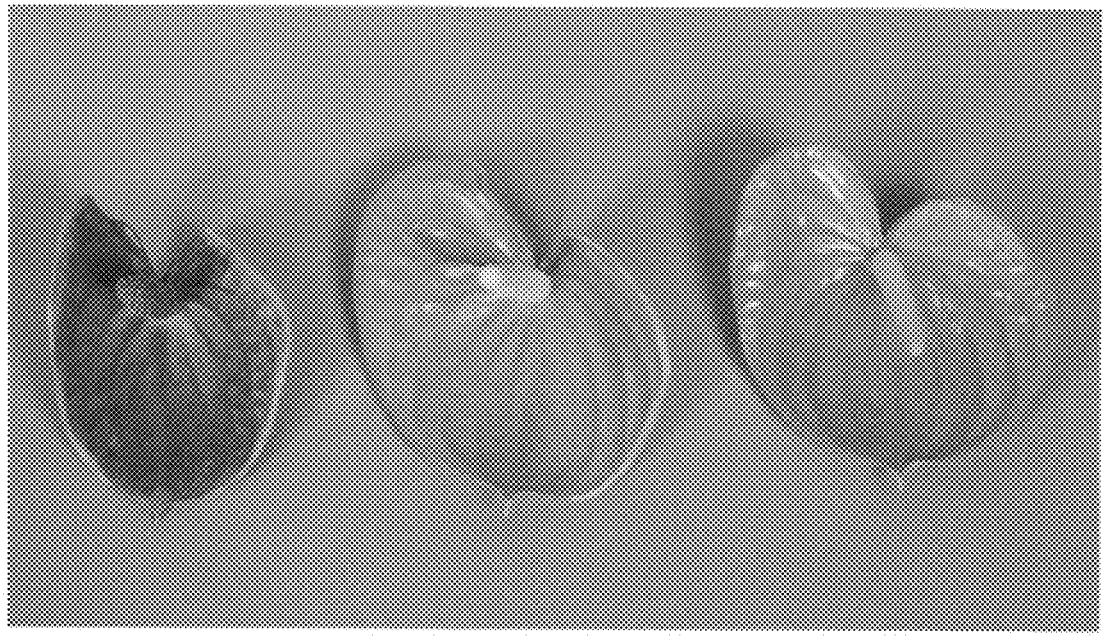
FIG. 3 shows three spathes at different stages of development, from left to right: 16 weeks, 8 weeks and just unfurled.
Figure 4:
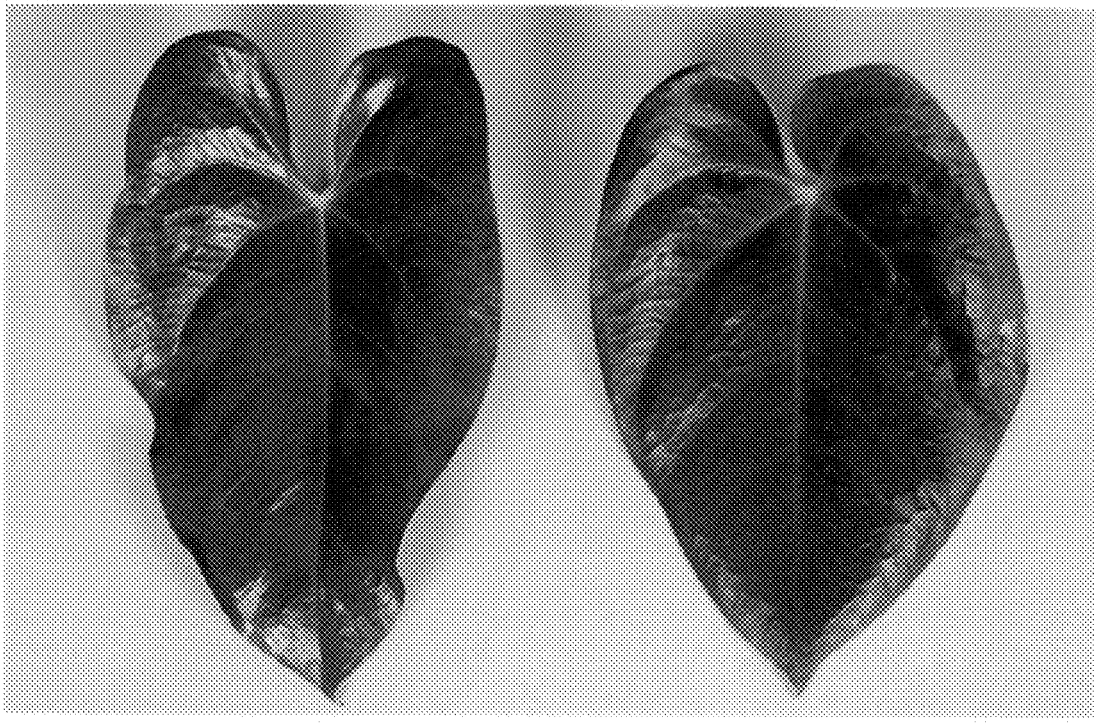
FIG. 4 shows the upper leaf surfaces: left side, just unfurled and right side, 10 weeks old.

The following detailed description sets forth the distinctive characteristics of 'Anthcaszim'. The data which define these characteristics were collected from asexual reproductions carried out in Bleiswijk, The Netherlands. The plant history was taken on 48-week old plants which were planted from tissue culture in 17 centimeter pots and grown in a glass greenhouse between 19° C. and 24° C. Observations were made in November of 2009. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

Parentage: Single plant mutation selected within a planting of the production clone of *Anthurium* 'Anthbneq'.

Plant:

*Propagation*.—Tissue culture.

*Root description*.—Fleshy cream-colored roots with smaller hairy lateral roots having yellow-colored root tips.

*Time to produce a finished flowering plant*.—50 to 55 weeks for a 17 cm pot.

*Growth habit*.—Herbaceous perennial.

*Height* (*measured from soil, including inflorescence*).—40.0 cm to 55.0 cm.

*Width* (*measured from leaf tips*).—50.0 cm to 60.0 cm.

Leaves:

*Immature leaves*.—Length: 13.0 cm to 18.0 cm. Width: 6.0 cm to 11.0 cm. Color: Upper surface: RHS 141B. Lower surface: RHS 146C. Texture (on both surfaces): Shiny.

*Mature leaves*.—Length (fully expanded): 15.0 cm to 23.0 cm. Width: 8.0 cm to 12.0 cm. Shape: Eliptical-cordate, slightly cupped. Apex: Acuminate. Base: Cordate. Leaf blade angle with the petiole: Between 110 degrees and 140 degrees. Leaf margin: Entire. Color: Upper surface: RHS 136A. Lower surface: RHS 137C. Texture (on both surfaces): Shiny, leathery and thick; very little to no blistering. Venation: Pinnate with protruding primary and mid-veins at the underside of the leaf blade. Venation color: Upper surface: RHS 137C. Lower surface: RHS 146C.

*Lobes*.—Arrangement: Leaf blade has two big lobes extending past the petiole. Length of lobes of mature leaf blades: 3.0 cm to 5.0 cm. Width of lobes of mature leaf blades: 4.0 cm to 6.0 cm. Distance for petiole/leaf junction to highest point on lobes of mature leaf blades: 4.5 cm to 6.5 cm.

*Petiole*.—Cross-section: Round. Diameter: 0.4 cm to 0.6 cm. Length: 16.0 cm to 22.0 cm on a mature leaf size. Color: Mature leaf: RHS 138A. Immature leaf: RHS 146C. Cataphyl color surrounding the petiole: Outside: RHS 146C, with a pale pink tinge at the base. Inside: RHS 147C.

*Geniculum*.—Length: 1.5 cm to 2.5 cm. Width: 0.5 cm to 0.6 cm. Color: RHS 138A.

Inflorescence:

*Arrangement*.—Single.

*Flowering habit* (*length of flowering season*).—Continuous.

*Number of inflorescences per plant*.—6 to 10.

*Fragrance*.—Absent.

*Longevity of inflorescence on plant*.—Up to a year.

*Longevity of the flower as a cut flower*.—Not observed.

Spathe:

*Buds*.—The spathe is tightly rolled around the spadix and extrudes from the peduncle sheath. After the spathe is fully opened the peduncle elongates some extra centimeters.

*Arrangement*.—Spathe angle with the peduncle is between 90 degrees and 110 degrees; the spathe stands on a wiry peduncle about 2.0 cm to 5.0 cm above the foliage.

*Shape*.—Ovate.

*Apex*.—Mucronate.

*Base*.—Cordate.

*Texture*.—Shiny to very slightly blistered.

*Margin*.—Entire.

*Size*.—Height: 24.0 cm to 30.0 cm (peduncle length at maturity). Length: 9.0 cm to 12.0 cm. Width: 8.0 cm to 10.0 cm.

*Color*.—Just fully open: Upper surface: RHS 58B. Lower surface: RHS 58D. 6 to 8 weeks after opening: upper surface, RHS 58B; lower surface, 39C. 12 to 14 weeks after opening: Upper surface, RHS 181A. The color slowly turns brown completely originating from the lobes towards the tip. The primary color becomes brown (approximately RHS 181 A). Lower surface, RHS 173D and 165A.

Peduncle:

*Shape*.—Erect.

*Cross-section*.—Round.

*Length*.—18.0 cm to 30.0 cm.

*Diameter*.—0.4 cm to 0.6 cm.

*Color*.—RHS 146B at unrolling of spathe and remaining the same color over time.

Flowering time:

*General*.—One small rooted untreated tissue culture plant of 2 cm tall will flower, depending on season, after 6 to 8 months and 2 to 3 blossoms appear. More blossoms appear after some additional weeks so that a full flowering and commercial plant will have 6 to 10 pink spathes. Smaller blossoms may occur on less mature plants.

Spadix:

*Size*.—Length: 3.0 cm to 5.0 cm (depending on flower size). Width (at apex): 0.5 cm to 0.7 cm. Width (at base): 0.7 cm to 0.9 cm.

*Shape*.—Columnar.

*Angle of spadix tip with peduncle*.—160-180 degrees (spadix is almost in one line with peduncle).

*Texture*.—When the spathe is unfurling the spadix is smooth. When the spadix matures, very small stigmata protrude. The stigmata are evenly distributed round the spadix. The spadix matures from base to top, slowly giving the spadix a somewhat rough appearance.

*Color*.—Immature: RHS 13A. Mature: RHS 155A. Ages to: RHS 146C.

Flowers:

*Quantity per spadix*.—200 to 260.

*Spadix flower arrangement*.—Bisexual, rounded in cross-section.

*Shape*.—Rounded.

*Size*.—Length: 0.1 cm to 0.2 cm. Diameter (maximum): 0.2 cm.

*Color*.—RHS 155A.

Reproductive organs:

*Stamens*.—None visible.

*Pollen*.—Sparse.

*Pollen color*.—RHS 156D.

*Pistil*.—Quantity: Many. Length: Less than 0.01 cm. Color: RHS 155A. Style: None observed.

*Stigma*.—Shape: Ovoid. Diameter: Less than 0.01 cm. Color: RHS 155A.

*Ovary*.—Rarely visible.

*Ovary color*.—RHS 155A.

Fruit and seed set: None observed.

COMPARISON WITH PARENTAL AND COMMERCIAL VARIETIES

'Anthcaszim' differs from the original variety 'Anthbneq' in having pink spathes whereas 'Anthbneq' has red spathes.

'Anthcaszim' is comparable to commercial varieties 'Pink Champion' (U.S. Plant Pat. No. 12,115) and 'Anthbneq' (U.S. Plant Pat. No. 15,286)

'Anthcaszim' differs from the commercial variety 'Pink Champion' in that 'Anthcaszim' has wider spathes than 'Pink Champion'.

TABLE 1

Comparison of characteristics between 'Anthcaszim', 'Pink Champion' and 'Anthbneq'

| Characteristic | 'Anthcaszim' | 'Pink Champion' | 'Anthbneq' |
|---|---|---|---|
| Spathe width | 8.0-10.0 cm | 5.0-8.0 cm | 8.0-10.0 cm |
| Color of spadix (ripe portion) | RHS 155 | RHS 48B | RHS 155 |
| Color of spathe | RHS 58B | RHS 52B | RHS 45A |

I claim:

1. A new and distinct variety of *Anthurium* plant named 'Anthcaszim' as shown and described herein.

* * * * *